US009084798B2

(12) United States Patent
Lin et al.

(10) Patent No.: US 9,084,798 B2
(45) Date of Patent: Jul. 21, 2015

(54) **USE OF LANOSTANE AND *PORIA* EXTRACT IN TREATING DIABETES**

(75) Inventors: Hang-Ching Lin, Taipei (TW); Yu-Chuan Huang, Taipei (TW); Tsu-Chung Chang, Taipei (TW); Wen-Liang Chang, Taipei (TW)

(73) Assignee: Sinphar Tian-Li Pharmaceutical Co., Ltd (Hangzhou), Zhejiang (CN)

( * ) Notice: Subject to any disclaimer, the term of this patent is extended or adjusted under 35 U.S.C. 154(b) by 557 days.

(21) Appl. No.: 12/854,037

(22) Filed: Aug. 10, 2010

(65) Prior Publication Data

US 2011/0053899 A1  Mar. 3, 2011

(30) Foreign Application Priority Data

Aug. 28, 2009  (CN) .......................... 2009 1 0168119

(51) Int. Cl.
| | | |
|---|---|---|
| *A01N 43/00* | (2006.01) | |
| *A61K 31/33* | (2006.01) | |
| *A01N 45/00* | (2006.01) | |
| *A61K 31/56* | (2006.01) | |
| *A61K 31/575* | (2006.01) | |
| *A61K 36/076* | (2006.01) | |

(52) U.S. Cl.
CPC ............. *A61K 31/575* (2013.01); *A61K 36/076* (2013.01)

(58) Field of Classification Search
USPC .................................................. 514/183, 170
See application file for complete search history.

(56) References Cited

U.S. PATENT DOCUMENTS

| | | | |
|---|---|---|---|
| 6,093,403 A | 7/2000 | Huo et al. | |
| 6,153,632 A * | 11/2000 | Rieveley | 514/369 |
| 7,056,734 B1 * | 6/2006 | Egan et al. | 435/325 |
| 7,094,763 B2 * | 8/2006 | Rybczynski et al. | 514/23 |
| 2004/0229852 A1 | 11/2004 | Lin et al. | |

FOREIGN PATENT DOCUMENTS

JP     10-330266     * 12/1998

OTHER PUBLICATIONS

Sato et al. "Dehydrotrametenolic Acid Induces Preadipocyte Differentiation and Sensitizes Animal Models of Noninsulin-Dependent Diabetes Mellitus to Insulin" Biol. Pharm. Bull. 25(1):81-86 (2002).
Liou et al. "Corni Fructus as the Major Herb of Die-Huang-Wan for Lowering Plasma Glucose in Wistar Rats" Journal of Pharmacy and Pharmacology 56:1443-1447 (2004).

* cited by examiner

*Primary Examiner* — Marcos Sznaidman
(74) *Attorney, Agent, or Firm* — Cesari and McKenna, LLP

(57) ABSTRACT

A pharmaceutical composition for treating diabetes is provided in this invention. The composition contains a lanostane compound as a potent component. A suitable source of the lanostane compound is a *Poria* extract from metabolite, sclerotium, or fermentation product of *Poria cocos* (Schw) Wolf. The *Poria* extract contains 1-60% of the lanostane compounds by weight of the extract, and is devoid of secolanostane.

13 Claims, 14 Drawing Sheets

R₁: COCH₃ (PA)

R₁: H (TA)

R₂: ◀OCOCH₃ (DHPA)

R₂: ◀OH (DHTA)

R₂: =O (PPA)

R₂: ⋯OH (EDHTA)

USE OF LANOSTANE AND *PORIA* EXTRACT IN TREATING DIABETES

CROSS-REFERENCE TO RELATED APPLICATIONS

This application claims the benefit of Chinese Application No. 200910168119.9, filed on Aug. 28, 2009, the content of which is hereby incorporated by reference in its entirety.

FIELD OF THE INVENTION

The present invention relates to a use of *Poria* extract in treating diabetes, and more particularly to a use of *Poria*-extracted compounds in treating diabetes induced from insufficient insulin in blood.

DESCRIPTION OF PRIOR ART

Diabetes mellitus is a chronic disease commonly seen in the adult population (especially the elderly people) of wealthy nations. Patients with diabetes can be mainly divided into two types, first of which is called Type I Diabetes or Insulin Dependent Diabetes Mellitus; the disease is resulted from the destruction of pancreatic β-cells by autoimmune responses in the human body, which leads to the inability to produce insulin in a patient's body. Therefore, these patients do not have insulin in their blood circulation, and require insulin injection consequently. The second type of diabetes is called Type II Diabetes or Non-Insulin Dependent Diabetes Mellitus, and the cause of the disease is still unclear, though genetic factors are thought to play an important role here, and influences of lifestyle (eg. obesity) is also vital in the induction of the disease.

In the year of approximately 500 A.D., a Chinese medical literature named "Emergency Formulas Worth a Thousand in Gold" was completed in the Tang Dynasty, which recorded many mixture of medicines used to treat diabetes, and some of the mixtures are known to comprise *Poria*. In 2002, a Japanese researcher named M. Sato published a paper in the Biological & Pharmaceutical Bulletin, which indicated that dehydrotrametenolic acid from the peels of *Poria* could be applied in the treatment of Type II Diabetes (Biol. Pharm. Bull. 2002, 25(1), 81-86). The underlying mechanism of which is to increase the sensitivity of a patient's body to insulin (which is equivalent to reducing a patient's resistance to insulin), thereby achieving the purpose of treating diabetes. However, past experiments using in vitro adipocytes had revealed that the effective concentration of dehydrotrametenolic acid is $10^{-5}$ M, and in vivo experiments involved the use of mice had indicated that the effective dose of dehydrotrametenolic acid is 110 mg/kg, which consequently made researchers reach the conclusion that an effective dose for use in the human body should be at least more than 700 mg. But the effective dose of 700 mg is equivalent to more than ten times the clinical dose used currently, which poses a real challenge to the development of clinical drugs thereof.

SUMMARY OF THE INVENTION

A purpose of the present invention is to disclose a method of treating diabetes, comprising administering to a mammal in need thereof an effective amount of a lanostane compound having the following chemical formula (I), or a pharmaceutically acceptable salt thereof, wherein the diabetes is induced from insufficient insulin in blood of the mammal.

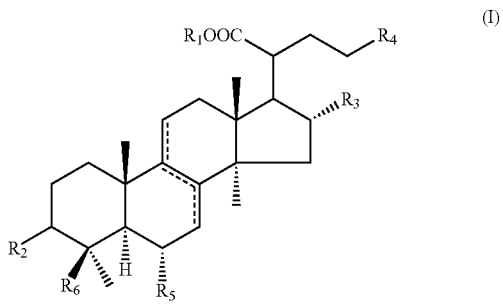

(I)

In the formula; $R_1$ can be either —H or —$CH_3$; $R_2$ can be —$OCOCH_3$, =O, or —OH; $R_3$ can be —H or —OH; $R_4$ can be —C(=$CH_2$)—C($CH_3$)$_2R_a$, wherein $R_a$ is either —H or —OH, or —CH=C($CH_3$)$R_b$, wherein $R_b$ is —$CH_3$ or —$CH_2OH$; $R_5$ is either —H or —OH, and $R_6$ is either —$CH_3$ or —$CH_2OH$.

Preferably, the method of the present invention comprises administering to the mammal an isolated lanostane compound having the formula (I) or a pharmaceutically acceptable salt thereof together with a pharmaceutical acceptable carrier or diluent.

The invention shows that the effective components extracted from *Poria* may functionally serve as insulin by: (1) increasing the gene expression (mRNA expression) of glucose transporter 4 (GLUT4); (2) increasing the production of GLUT4; (3) intracellularly translocating the GLUT4 proteins onto the cell membrane of lipid (or muscle) cells; (4) allowing GLUT4 to transport extracellular glucose into the cells, and (5) manufacturing and storing triglycerides in the cells like insulin does. Therefore, the effective components of *Poria* may functionally serve as insulin, and transport glucose from the blood stream into the cells, which in turn lowers blood glucose levels. As a result, said components are ideal to be applied in the treatment of Type I Diabetes and Type II Diabetes caused by insufficient blood insulin. More importantly, in vitro lipid experiments had indicated that said components can induce glucose absorption at the concentration of 0.01 μM, which is 1000 times less than the effective concentration of $10^{-5}$ M described by the Japanese researcher Sato.

The present invention also discloses a method of treating diabetes, comprising administering to a mammal in need thereof an effective amount of a *Poria* extract, wherein said *Poria* extract comprises, based on the weight of the *Poria* extract, 1-60% of a lanostane compound having the chemical formula (I) defined as above, and said *Poria* extract is substantially free of secolanostane, wherein the diabetes is induced from insufficient insulin in blood of the mammal.

Preferably, said *Poria* extract comprises, based on the weight of the *Poria* extract, 5-35% of the lanostane compound (I).

Preferably, the lanostane compound (I) has the following chemical formula:

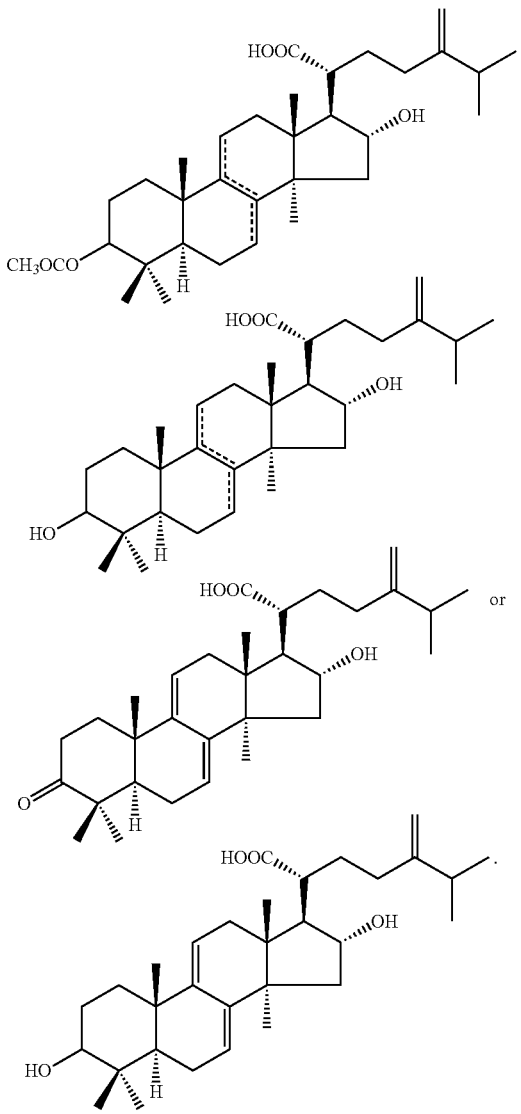

More preferably, the lanostane compound (I) has the following chemical formula:

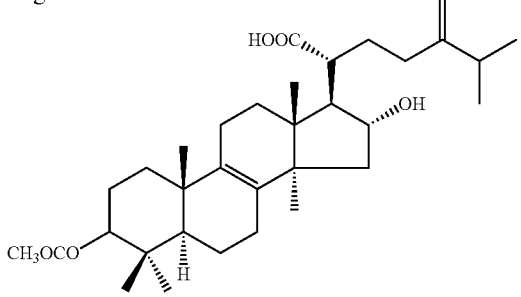

Preferably, the administering is injection.
Preferably, the administering is oral intake.
Preferably, the diabetes is type I diabetes.
Preferably, the diabetes is type II diabetes.
Preferably, the mammal is a human.

BRIEF DESCRIPTION OF DRAWINGS

The aforesaid objectives and advantages of the present invention will be more clearly understood when considered in conjunction with the accompanying drawings, in which.

DETAILED DESCRIPTION OF PREFERRED EMBODIMENTS

Figure 1:
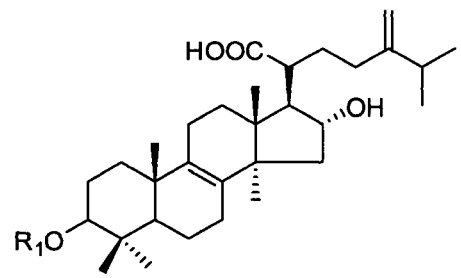
FIG. 1 is a diagram that shows the structure of lanostane-type triterpene compounds extracted and purified from *Poria*.
Figure 1:
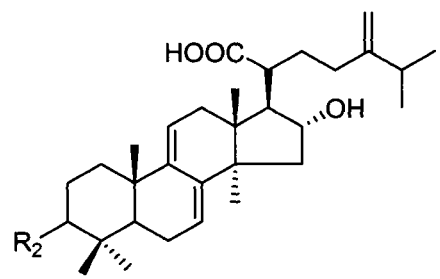

An extract of *Poria* for enhancing nutrient uptake by mammals (for example, humans) disclosed in the present invention can be prepared by a process similar to that disclosed in US2004/0229852 A1, which includes extracting *Poria cocos* (Schw) Wolf with the conventional extraction methods to obtain a crude extract, separating the crude extract by chromatography into a low polarity fraction of lanostane (with an eluent of dichloromethane:methanol of 96:4) and a high polarity fraction of secolanostane (with eluents of dichloromethane:methanol of 90:10, and 0:100), wherein the lanostane fraction is detected by a thin layer chromatography having a chromatographic value, Rf, not less than 0.1 in accordance, when it is developed by a mixed solvent of dichloromethane:methanol=96:4; the Rf is less than 0.1 for the secolanostane fraction. Several lanostanes are separated from the lanostane fraction by subjecting the lanostane fraction to silica gel column chromatography eluted, wherein the eluents used are dichloromethane:methanol=97:3 to 95:5.

The following examples are provided for describing the present invention in further details, but should not be used to limit the scope of the present invention.

Percentages and other amounts referred to in this specification are by weight unless indicated otherwise. Percentages are selected from any ranges used to total 100%.

Example 1

26 kg of *Poria* grown in Yunnan was extracted with 260 liters of 75% aqueous alcohol solution under heating. The extraction were repeated three times; the resulting three extraction solutions were combined and vacuum concentrated to yield an extract of 225.2 g. Quantitative analyses were subsequently carried out on the extract, which indicated that 76.27 mg of lanostanes could be found in every gram thereof, wherein K1 (pachymic acid) took up 33.4 mg; K1-1 (dehydropachymic acid) took up 9.59 mg; K2-1 (tumulosic acid) occupied 19.01 mg; K2-2 (dehydrotumulosic acid) occupied 6.75 mg; K3 (polyporenic acid C) occupied 5.06 mg, and K4 (3-epidehydrotumulosic acid) occupied 2.46 mg.

Example 2

125 g of the alcohol extract from Example 1 was further extracted six times with 1.3 liters of dichloromethane; the resulting six extraction solutions were combined and concentrated to obtain an extract of 22.26 g. The dichloromethane extract were dissolved in heated 95% alcohol and left to cool, followed by filtering and discarding the insoluble substances. A small amount of water was added into the filtrate until the alcohol concentration reached 45% therein, which resulted in precipitation; from which a precipitate of 17.4 g was obtained by centrifugation consequently. Subsequent quantitative analyses on the precipitate indicated that each gram thereof comprised 264.78 mg of lanostanes, wherein K1-1 occupied 159.7 mg; K1-2 occupied 56.96 mg; K2-1 occupied 24.43 mg; K2-2 occupied 8.8 mg; K3 occupied 9.84 mg, and K4 occupied 5.05 mg. The method of thin layer chromatography (TLC) with silica gel was used to confirm the precipitate did not comprise any secolanostane.

Example 3

100 kg of *Poria* was boiled with 800 kg of water for 3 hours, then left for cooling to 50° C. and a pH value thereof was adjusted to pH 11 by using a 5N NaOH solution, followed by stirring the resulted solution for 3 hours. A centrifugation machine was used to separate the liquid from the solid, followed by adding another 800 kg of water to the separated solids. The aforesaid procedures were repeated, including adjusting pH value with NaOH to pH 11, stirring, and removing the solids by centrifugation. The two resulting liquids were combined, and then vacuum concentrated to a solution of 100 kg at 50° C., followed by the adjustment of pH value to pH 6.5 by using 3N HCl so as to produce a precipitate. Said precipitate was separated from the solution, subsequently rinsed with 40 L H2O, and centrifuged in order to recover the precipitate; the precipitate was sprayed dry with 8 L of water, which yielded 380 g of powder. Afterwards, the powder was extracted three times by using 4 L of alcohol, and the extraction solutions were combined and concentrated to result in 238.9 g of alcohol extract. The 238.9 g of alcohol extract was proved containing no secolanostane compounds by the TLC analysis, and then was subjected to HPLC separation, which gave 214 mg of K2, 23 mg of K3, 24 mg of K4, and 4.52 mg of K1 in per gram of the extract. In other words, each gram of the extract has approximately 265 mg of lanostane compounds.

Or the powder was extracted by using 4 L of 50% aqueous alcohol solution, and then had the 50% aqueous alcohol solution removed in order to obtain an insoluble powder; the extraction was repeated three times to yield 245.7 g of a substance insoluble in 50% aqueous alcohol solution. The insoluble substance was confirmed having no secolanostane compounds by the TLC analysis, and then underwent separation and purification processes by HPLC, which yielded 214 mg of K2, 23 mg of K3, 24 mg of K4, and 4.52 mg of K1 in each gram of the extract, which is equivalent to approximately 261 mg of lanostane compounds in each gram of the extract.

Example 4

A *Poria* powder was made of 30 kg of the China-grown *Poria cocos* (Schw) Wolf. The *Poria* powder was extracted with 120 L 95% alcohol for 24 hours. The mixture was filtered to obtain a filtrate. The residue was extracted and filtered for another three cycles. The filtrates were combined and concentrated to bring about a dried extract in an amount of 265.2 g. The dry extract underwent a distribution extraction with a two-phase extraction agent (n-hexane: 95% methanol=1:1), and the methanol layer was removed therefrom, which is then concentrated to obtain a dry solid in an amount of 246.9 g. A separation of the dry solid was carried out by means of a silica gel column, which was filled with silica gel 10-40 times of the weight of the dry solid. The silica gel having a diameter of 70-230 mesh was made by Merck Corporation with a code of Silica Gel 60. The column was eluted by the following eluates in sequence: a mixed solvent of dichloromethane:methanol=96:4; a mixed solvent of dichloromethane:methanol=90:10, and pure methanol. The eluates were tested by the thin layer chromatography (TLC), wherein an ultraviolet lamp and iodine vapor were used for detecting, and a mixed solvent of dichloromethane:methane=96:4 was used as a developing liquid. The eluates having similar constituents in the TLC were combined.

The elution carried out with the mixed solvent of dichloromethane:methanol=96:4 resulted in a PCM portion in an amount of 78 g. The PCM showed 6 trace points in the thin layer chromatography. The resulted eluates from the elutions carried out with the eluents of dichloromethane:methanol=90:10 and pure methanol were combined to obtain a PCW portion in an amount of 168 g.

The PCM portion was further separated by means of an eluent of dichloromethane:methanol=96.5:3.5 and the same silica gel column to obtain purified lanostane components of K1 (K1-1 and K1-2), K2 (K2-1 and K2-2), K3, K4, K4a, K4b, K5, K6a and K6b. Further details of the separation steps and identification analysis data can be found in US2004/0229852 A1.

The aforesaid K1 to K6b compounds have the following structures:

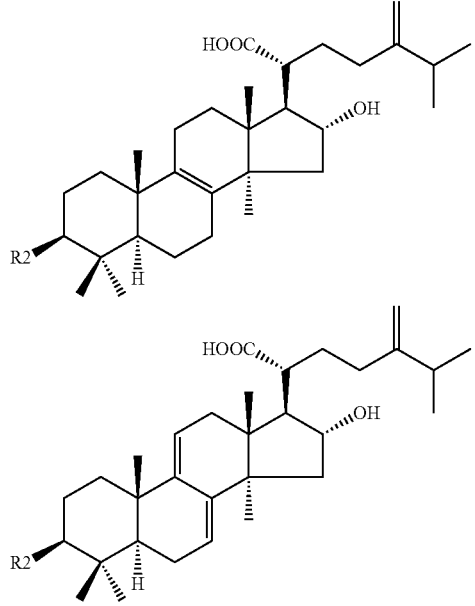

K1-1: R2=OCOCH3 (pachymic acid) K1-2: R2=OCOCH3 (trace quantity)

K2-1: R2=OH (tumulosic acid) (dehydropachymic acid)

K2-2: R2=OH (trace quantity) (dehydrotumulosic acid)

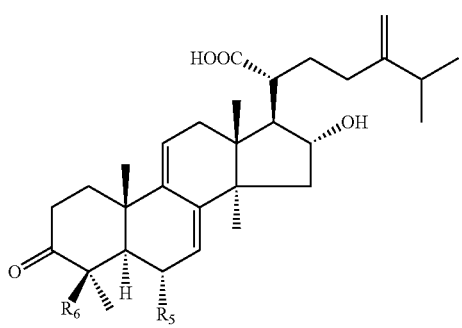

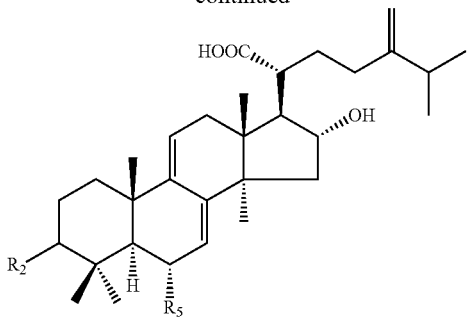

K3: R6=CH3, R5=H (polyporenic acid K4: R2=α-OH, R5=H C) (3-epidehydrotumulosic acid)
K4a: R6=CH$_2$OH, R5=H K4b: R2=β-OCOCH3, R5=OH
K6a: R6=CH3, R5=OH

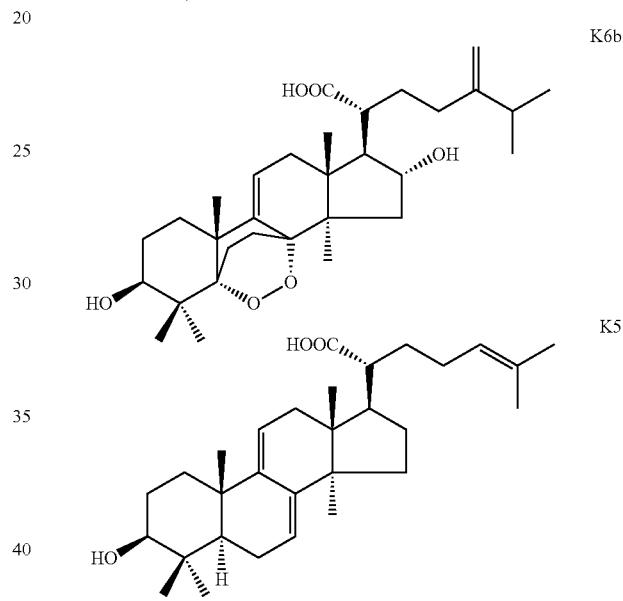

The amounts of the lanostane compounds K1 to K6b separated from the PCM portion are listed in the table below. The PCM portion contains approximately 15 wt % of the lanostane compounds K1 to K6b.

| K1 | K2 | K3 | K4 | K4a | K4b | K5 | K6a | K6b |
|---|---|---|---|---|---|---|---|---|
| 3.0 g | 6.2 g | 1.93 g | 0.55 g | 66 mg | 86.8 mg | 47.6 mg | 21.4 mg | 90.7 mg |

Example 5

Capsules having the PCM portion prepared in Example 4 were prepared basing on the following composition:

| Components | Per Capsule | Per 30,000 Capsules |
|---|---|---|
| PCM prepared in Example 4 (containing approximately 15 wt % of K1-K6 compounds) | 11.2 mg | 336.0 g |
| Sodium silicoaluminate | 5.0 mg | 150.0 g |

| Components | Per Capsule | Per 30,000 Capsules |
|---|---|---|
| Starch Potato | 378.8 mg | 11,364.0 g |
| Magnesium Sterate | 5.0 mg | 150.0 g |
| Total | 400 mg | 12,000.0 g |

The PCM portion and sodium silicoaluminate were sifted by using a #80 mesh, and the starch potato was sifted by using a #60 mesh; while magnesium sterate was sifted by using a #40 mesh. Subsequently, the aforesaid components were mixed evenly in a mixer, followed by filling the resulting mixture into No. 1 empty capsules. Each capsule contains approximately 1.68 mg (0.42 wt %) of effective components K1-K6.

Example 6

Experiments Testing the Use of Triterpene Compounds to Prevent and Treat Type I Diabetes The *Poria* extracts used for the following cell experiments were either the precipitate made in Example 2, or the purified compound shown in FIG. 1. The extracts were dissolved in a solvent made of alcohol:DMSO (9:1); the resulted solution was added into culture dishes, in which only one-thousandth of a final volume was added into each well.

1. Cell Culture of Adipocytes

3T3-L1 is a type of rodent preadipocytes that initially appear to be spindle-celled. When the cells are added with an inducing agent and cultured for 2-3 days, the cells are transformed and would appear more round in morphology; the more days the cells are allowed to differentiate, the more specialized the cells become. In cells that have not undergone differentiation, the main glucose transporter is GLUT1, whereas in differentiated cells, the main active glucose transporter is GLUT4. Moreover, the more GLUT4 on the cells' membrane, the faster and larger volume of blood glucose that are transferred across the cell membrane and absorbed by the cells, and thus blood glucose could be lowered more speedily. The 3T3-L1 adipocytes possess a comprehensive system of glucose absorption activated by insulin, and thus is adequate for the research of glucose metabolism and insulin signaling pathway, as well as for observing the complete process of the generation and regulation of lipids. Therefore, the fully differentiated 3T3-L1 adipocytes has become a representative cell strain that is applied widely, and because the real adipocytes from human tissues are difficult to culture in successive generations, researchers generally use this particular cell strain to carry out relevant experiments and evaluations.

(a) Cell Culture of Adipocytes

3T3-L1 preadipocytes were cultured in Dulbecco's minimal essential medium (DMEM) supplemented with 100 IU/mL penicillin, 100 g/mL streptomycin, 1% nonessential amino acid and 10% calf serum in 5% CO2 and 95% Air at 37° C. Once the cells have become fully grown, differentiation was induced by treating the cells with differentiation inducers (DMEM containing 0.5 mM 3-isobutyl-1-methylxanthane (IBMX), 1 M dexamethasone, 10 g/mL insulin, and 10% fetal bovine serum) for two days. The cells were re-fed with DMEM supplemented with 10 g/mL insulin and 10% FBS for another two days, and then changed to 10% FBS/DMEM without insulin every 2 days for 4-6 days. At this stage, near 90% of the cells expressed the adipocyte phenotype and were ready for the experiments. Before commencing the experiments, the 3T3-L1 cells were rinsed with PBS solution first, and then cultured overnight in the serum-free and insulin-free 0.2% BSA/DMEM culture medium, so as to remove interferences from both serum and insulin.

(b) Cell Culture of Adipocytes Used for Inhibited mRNA Expression of GLUT4 Experiments A viral carrier (TRCN0000043630 shRNA, Genomics Research Center, Academia Sinica, R.O.C.) carrying GLUT4-inhibiting RNA was used to infect the 3T3-L1 preadipocytes (shG4-30), in order to create a gene expression having consistent inhibition of GLUT4 expression, and the cell strain was allowed to further differentiate, from which the differentiated adipocytes were used for the experiments.

(c) Cell Culture of Adipocytes Used for Testing Translocation of GLUT4 Proteins:

A GLUT4 carrier with the influenza viral protein HA marking (donated by HA-GLUT4-GFP, Timothy E. McGraw, Weill Cornell Medical College) was used to transfect the 3T3-L1 preadipocytes by Lipofectamine 2000 (Invitrogen, CA, USA), and strains of adipocytes that consistently expressed GLUT4 proteins with the influenza viral protein HA marking were screened by using G418, so that the cells were allowed to differentiate into adipocytes and used for evaluating the translocation of GLUT4 proteins.

2. Evaluation of 2-Deoxy-Glucose Uptake

For the experiment of testing the effects of triterpene compounds on enhancing glucose uptake by 3T3-L1 adipocytes, 3T3-L1 preadipocytes were cultured on 6-well culture dishes, and allowed to grow fully therein before being subjected to differentiation by a differentiation-inducing agent. Once the 3T3-L1 cells became matured and differentiated into adipocytes after 7-12 days, the cells were used for testing glucose uptake. Said adipocytes were firstly placed in a serum-free culture medium (0.2% BSA/DMEM) overnight, followed by cultivation for 2-6 hours in serum-free cell culture media containing different concentrations of triterpene compounds, and then rinsed once with PBS solution before undergoing cultivation in KRP buffer (20 mM HEPES, 137 mM NaCl, 4.7 mM KCl, 1.2 mM $MgSO_4$, 1.2 mM $KH_2PO_4$, 2.5 mM $CaCl_2$, and 2 mM pyruvate, pH 7.4 and 0.2% BSA) at 37° C. for 3 hours. Finally, 0.2 µCi/mL of 2-deoxy-D-[$^{14}$C]-glucose (2-DG, Amersham Biosciences, Little Chalfont, Bucks, U.K) and 0.2 ml of non-radioactive glucose buffer derived from 0.1 mM 2-DG were used as a substitute for KRP buffer in order to begin the experiment on glucose uptake. After allowing the experiment to run for minutes, the cells were removed and rinsed with PBS solution to terminate the intake of glucose. Subsequently, the cells were dissolved in 0.2 ml of 0.2% SDS, and 10 µL, of the solution with dissolved cells was transferred into UniFilter plates (Perkim-Elmer, Wellesley, Mass., USA) with filtering bases and dried in a vacuum oven at 37° C., in which each well was added with 30 µL of counting solution, and then analyzed by using a micro-disk liquid scintillation analyzer (TopCount, Packard NXT, Packard BioScience Company, Meriden, Conn., USA). The glucose concentration accumulated in the cells was calculated, and divided by the protein concentration, so as to obtain a glucose uptake rate indicated as nanomoles of glucose uptake in every microgram of cell proteins at every minute (nmol/min/mg). The protein concentration was determined by using the standard Bicinchoninic acid (BCA) protein assay kit (Pierce, Rockford, Ill., USA). The uptake of non-specific glucose was determined by adding 0.2 µCi of L-[14C]-glucose, and then used to substract from the value obtained by the analyzer so as to get a value for the uptake of specific glucose. Therefore, the effects of different concentrations of triterpene compounds on the glucose uptake by 3T3-L1 adipocytes could be determined.

3. Evaluation of GLUT 1 & 4 Proteins

For the experiment of testing the effects of triterpene compounds on enhancing the GLUT protein expression in 3T3-L1 adipocytes, the aforesaid differentiated and mature 3T3-L1 adipocytes were cultured overnight in a serum-free cell culture medium, and then further cultured in serum-free cell culture media containing different concentrations of triterpene compounds for 24 hours. This was followed by rinsing the cells with PBS solution, and allowing the cells to lyse in 0.2 mL lysis buffer (1% NP-40, 150 mM NaCl, 0.1% SDS, 50 mM Tris-HCl pH 7.6, 10 mM EDTA, 0.5% deoxycholate, 1 mM PMSF, 1 mM Na3VO4, 10 mM NaF, 10 mM β-glycerophosphate, 10 g/mL protease inhibitor and phosphotase inhibitor cocktails) for 30 min at 4° C. An equal amount of protein from each sample was separated by sodium dodecyl sulfate (SDS)-10% polyacrylamide gel electrophoresis (PAGE) and transblotted onto polyvinylidene difluoride (PVDF) membranes (Millipore, Bedford, Mass., USA). Subsequently, the Western blot analysis was carried out by using monoclonal antibodies targeted for GLUT1 (Abeam, Cambridge, Mass.), GLUT4 (R&D systems, Minneapolis, Minn.), and (β-Actin, Chemicon, Temecula, Calif., USA), so as to determine whether there was any effects on GLUT protein expression in 3T3-L1 adipocytes under different concentrations of triterpene compounds. Each sample of proteins was treated with a chemiluminescence kit (ECL, Amersham, U.K.) before being exposed and processed into X-ray film, and then quantitatively analyzed by using computer software.

4. Evaluation of Gene Expression of GLUT 1 & 4

Real-time Q-PCR was performed in order to evaluate mRNA expression of GLUT proteins in 3T3-L1 adipocytes under different concentrations of triterpene compounds. Firstly, the fully differentiated 3T3-L1 adipocytes were mixed with different concentrations of triterpene compounds and left for 24 hours, before removing the cell culture medium and using the Trizol buffer (Invitrogen, Irvine, Calif., USA) to obtain total RNA from the cells. Afterwards, 1 μg of RNA sample was taken therefrom, and a High-Capacity cDNA Reverse Transcription Kit (Applied Biosystems, Darmstadt, Germany) was used to reverse transcribe mRNA in the sample into cDNA. Primers were specifically designed for GLUT1, GLUT4, and β-actin, and the SYBR Green Q-PCR analyzer (Applied Biosystems, Foster City, Calif., USA) was used to expand the gene for detection (Glut1 & 4) and reference gene (β-actin), before relative gene expression values were calculated by the ΔΔCT method using the StepOne v2.0 software (Applied Biosystems).

5. Evaluation of Translocation of GLUT4 Proteins (1) Analysis of Translocation of GLUT4 Proteins In the mechanism of insulin enhancing glucose uptake by adipocytes or muscle cells, the translocation of GLUT4 from intracellular organelles to plasma membrane (PM) actually plays a vital rol therein, thus the effects of triterpene compounds on enhancing the translocation of GLUT4 to plasma membrane in 3T3-L1 adipocytes were tested here. The differentiated and mature 3T3-L1 adipocytes were cultured overnight in a serum-free cell culture medium, and then further cultured in serum-free cell culture media containing different concentrations of triterpene compounds for 2 hours. This was followed by high-speed centrifugation at different rotation speeds (16,000 g-200,000 g) in order to separate the cellular plasma membrane fraction from the low density microsome (LDM) [Liu, L. Z. et. al.; Mol. Biol. Cell 17, (5), 2322-2330, 2006]. Western blot analysis was performed by using a monoclonal antibody for GLUT4, so as to observe whether there are any effects from different concentrations of triterpene compounds on the translocation of GLUT4 from cellular LDM to PM in 3T3-L1 adipocytes.

(2) Analysis of Translocation of GLUT4 Proteins

3T3-L1 preadipocytes stably expressing HA-GLUT4-GFP were grown on 96-well culture dishes, and then allowed to differentiate by an inducing agent after becoming fully grown (Govers, R. et. al.; Mol Cell Biol. 24 (14), 6456-6466, 2004). The fully differentiated 3T3-L1 adipocytes were given and left with different concentrations of triterpene compounds for 2 hours, followed by removing the cell culture medium and rinsing the cells with ice-cold PBS solution. Subsequently, the cells were fixed in 4% paraformaldehyde at room temperature for 15 minutes, and then incubated with primary anti-hemagglutinin (HA) antibody (12CA5) for 2 hours after rinsing the cells with ice-cold PBS solution 2-3 times. Afterwards, the cells were again rinsed with ice-cold PBS solution 2-3 times, and incubated with rhodamine-conjugated secondary antibodies (Leinco, Ballwin, Mo.) for 1 hour. The cells were rinsed with ice-cold PBS solution again before measuring activated wavelength of fluorescence (Em. 480/Ex. 425 nm and Em. 576 nm/Ex. 550 nm) from rhodamine and GFP by using a fluorescence microtiter plate reader (POLARstar Galaxy; BMG Labtechnologies, Offenburg, Germany). The ratio of rhodamine fluorescence to GFP fluorescence was calculated, and used to evaluate a relative quantity of HA-GLUT4-GFP translocated to plasma membrane. Since HA-tagged GLUT4 could only be labelled by rhodamine after it has translocated to plasma membrane, the ratio was useful in the evaluation of GLUT4 translocation to plasma membrane.

6. Effects from the Accumulation of Triglycerides and the Release of Glycerol

For the experiment of testing the effects of triterpene compounds on the accumulation of triglycerides and the release of glycerol in 3T3-L1 adipocytes, the differentiated and mature 3T3-L1 adipocytes were cultivated overnight in a serum-free cell culture medium, and then further cultivated in serum-free cell culture media containing different concentrations of triterpene compounds for 24 hours. The culture media were collected and tested for the release of glycerol by using a glycerol assay kit (Randox Laboratories, Antrim, UK), to determine whether different concentrations of triterpene compounds had any effects on the release of glycerol from lipid breakdown in 3T3-L1 adipocytes. The level of triglycerides in the adipocytes were determined by Oil-Red O staining (Ramirez-Zacarias, J. L. et. al.; Histochemistry 97, (6), 493-497, 1992). The oil droplets formed by the accumulation of lipids in the cells were stained, rinsed twice with 60% isopropanol, and then extracted in 100% isopropanol before being quantified at the absorbance of 490 nm. The readings were compared with that from the adipocytes without being given triterpene compounds, in order to evaluate the effects of different concentrations of triterpene compounds on the accumulation of triglycerides in the adipocytes.

Figure 2A:
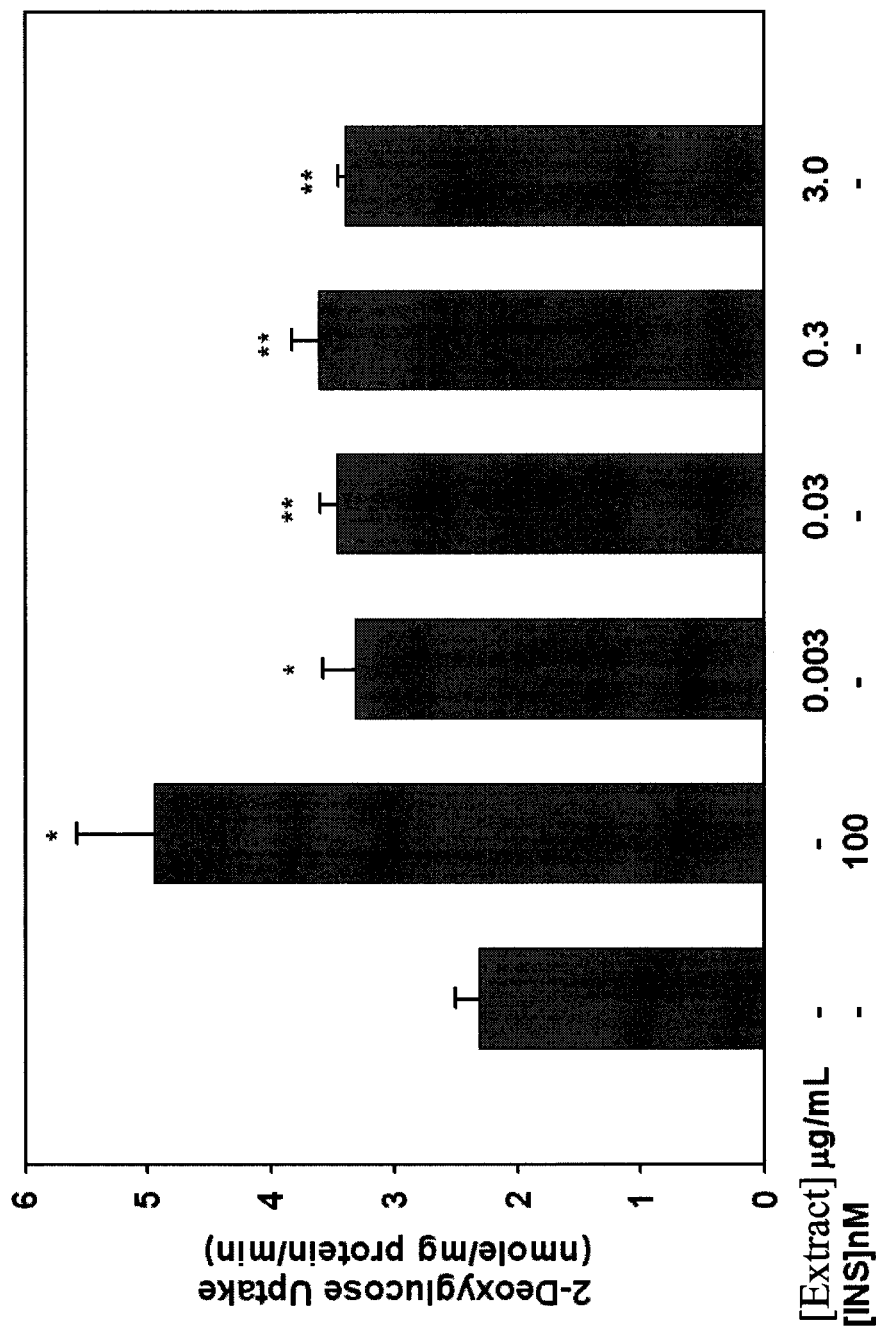
FIG. 2A is a plot that shows the effects *Poria* extracts had on enhancing sugar uptake by the 3T3-L1 adipocytes.
Figure 2B:
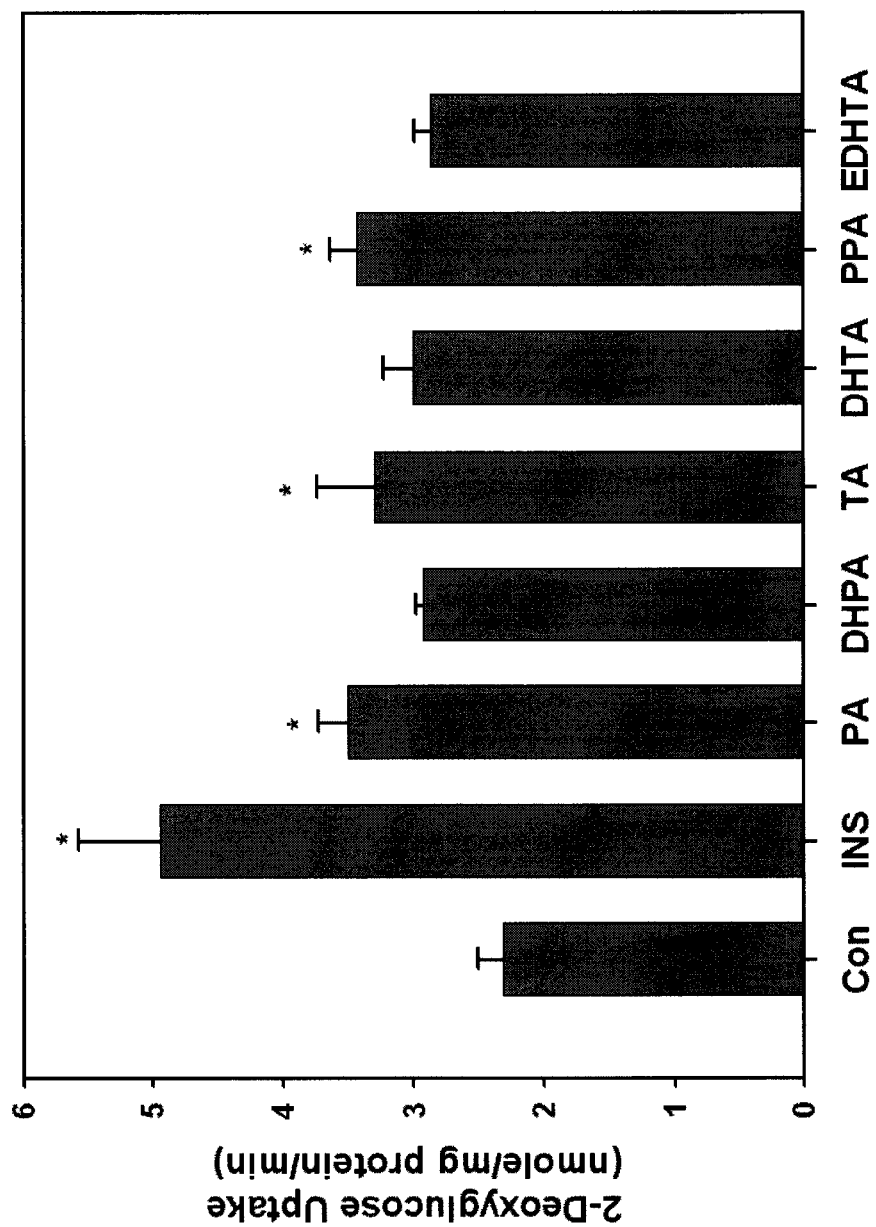
FIG. 2B is a graph that indicates the effects of allowing insulin (0.1 μM) to act for 30 mins and purified triterpene compounds (0.01 μM) to act for 2 hours had on sugar uptake under the condition of added sugar. The figures are shown as mean±SD (n=6). The symbol * is used to indicate p<0.05, and ** means p<0.01, in comparison with the control group (untreated).

The experimental results indicated that like insulin, the triterpene compounds possess the following four properties, and thus is effective for treating Type I Diabetes:

(1) In the Adipocyte Model, Components or Extracts from *Poria* were Effective for Enhancing the Absorption of Extracellular Glucose into the Cells:

From the evaluation of the effects of *Poria* extracts (Example 2) on mature adipocytes, as shown in FIG. 2A; *Poria* extracts were evidently effective for increasing glucose uptake, and the effect for increasing glucose uptake was positively correlated to increases in doses given to the cells. On the other hand, the addition of 100 nM of insulin was also effective for increasing glucose uptake. The pure compounds from Example 2 were used for further experiments. FIG. 2B showed that two hours after giving the pure compounds to the adipocytes, three of the compounds that included PA, TA, and PPA significantly increased glucose uptake to 165.89%, 142.5%, and 147.9% when given at 0.01 μM. Wherein the increase induced by PA was the most significant, thus the following evaluations were carried out by basing on PA.

Figure 3A:
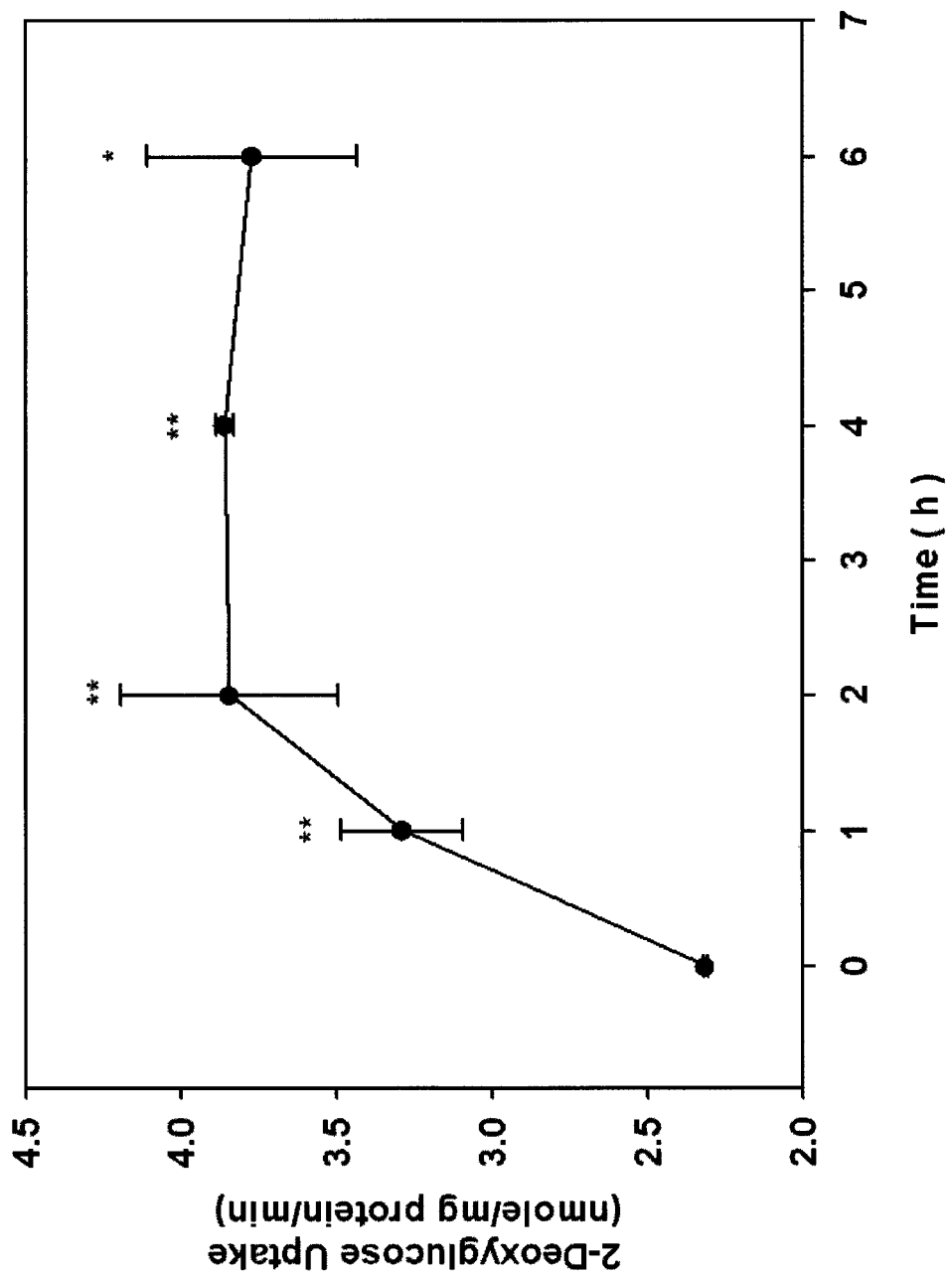
FIG. 3A is a plot that indicates pachymic acid (PA) was effective for inducing the highest sugar uptake rate when given at 0.01 μM for two hours.
Figure 3B:
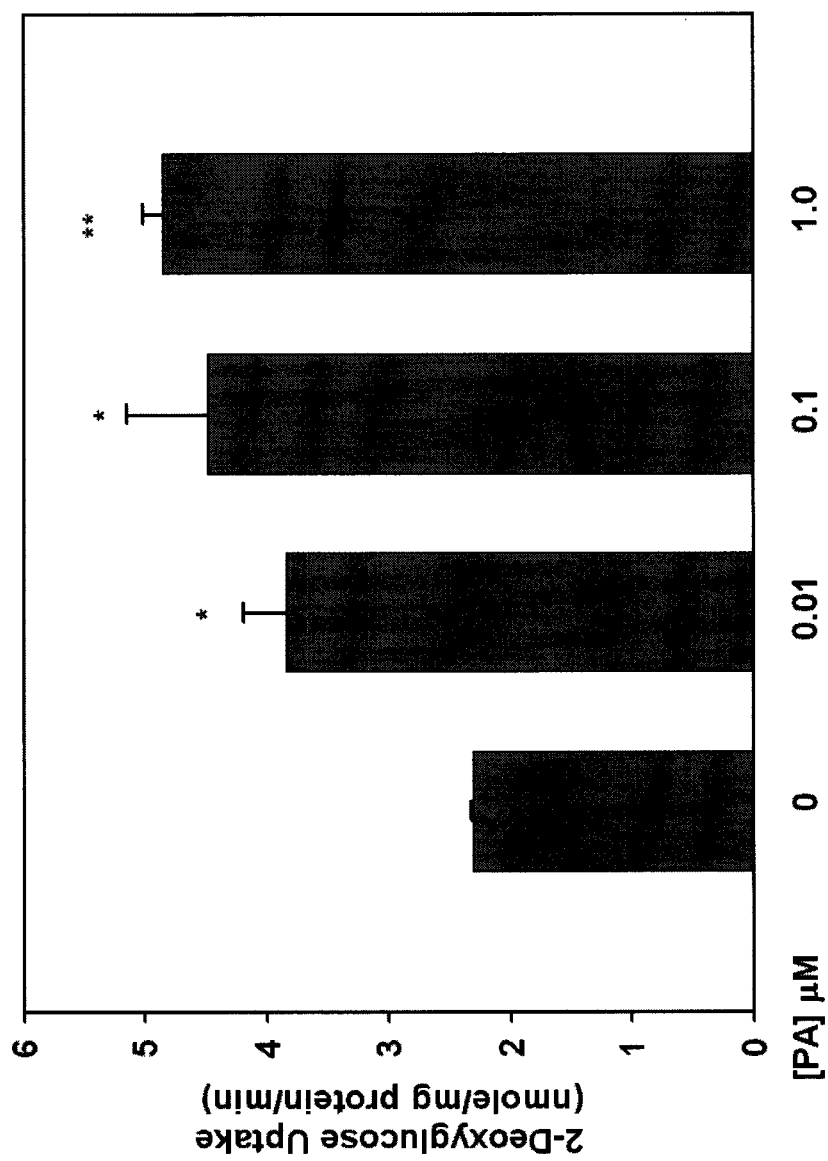
FIG. 3B is a graph that indicates an increase of sugar uptake along with an elevation of PA doses. PA was allowed to act for two hours before sugar was added for testing, and the figures are shown as mean±SD (n=6). The symbol * is used to indicate p<0.05, and ** means p<0.01, in comparison with the control group (untreated).

According to FIG. 3A, the effects of PA on increasing glucose uptake elevates along with the lapse of time, and was the most significant at 2 hours after being administered (increased to 165.89%). In addition, an increase of PA concentration led to elevated glucose uptake. It can be observed in FIG. 3B that when PA was given at 1 μM, the glucose uptake was increased to 209.84%.

Figure 4:
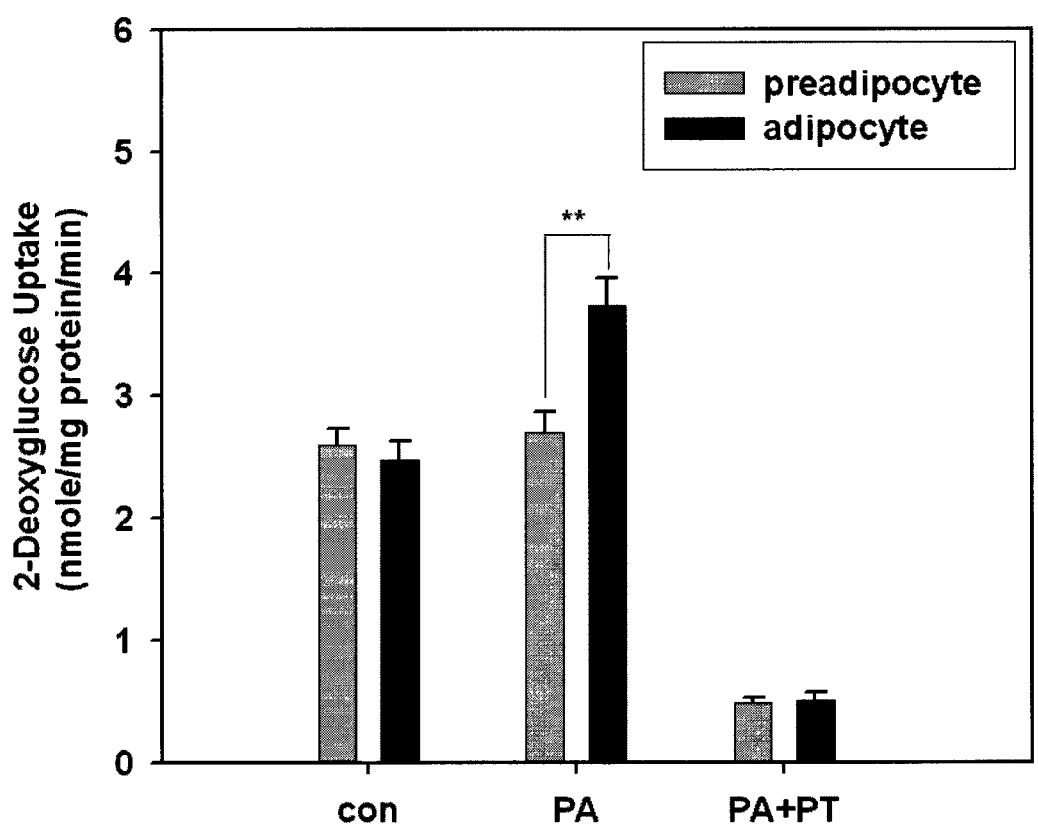
FIG. 4 is a plot that shows PA could only enhance sugar uptake in the differentiated and mature adipocytes. If immature and mature adipocytes were firstly mixed with PA and allowed to react for two hours, and then added with PT; the sugar uptake in said two types of cells would be significantly suppressed, as would the enhancement of sugar uptake by PA. The figures are shown as mean±SD (n=6). The symbol * is used to indicate p<0.05, and ** means p<0.01, in comparison with the control group (untreated).

According to FIG. 4, PA was only effective for enhancing glucose uptake in differentiated adipocytes, not for preadipocytes. When phloretin (PT) was administered to both preadipocytes and adipocytes, the glucose uptake in both types of cells were significantly inhibited. According to past research literature, the preadipocytes only possess GLUT1, whereas the adipocytes possess GLUT 4. Therefore, PA is thought to increase glucose uptake by increasing GLUT4.

Figure 5A:
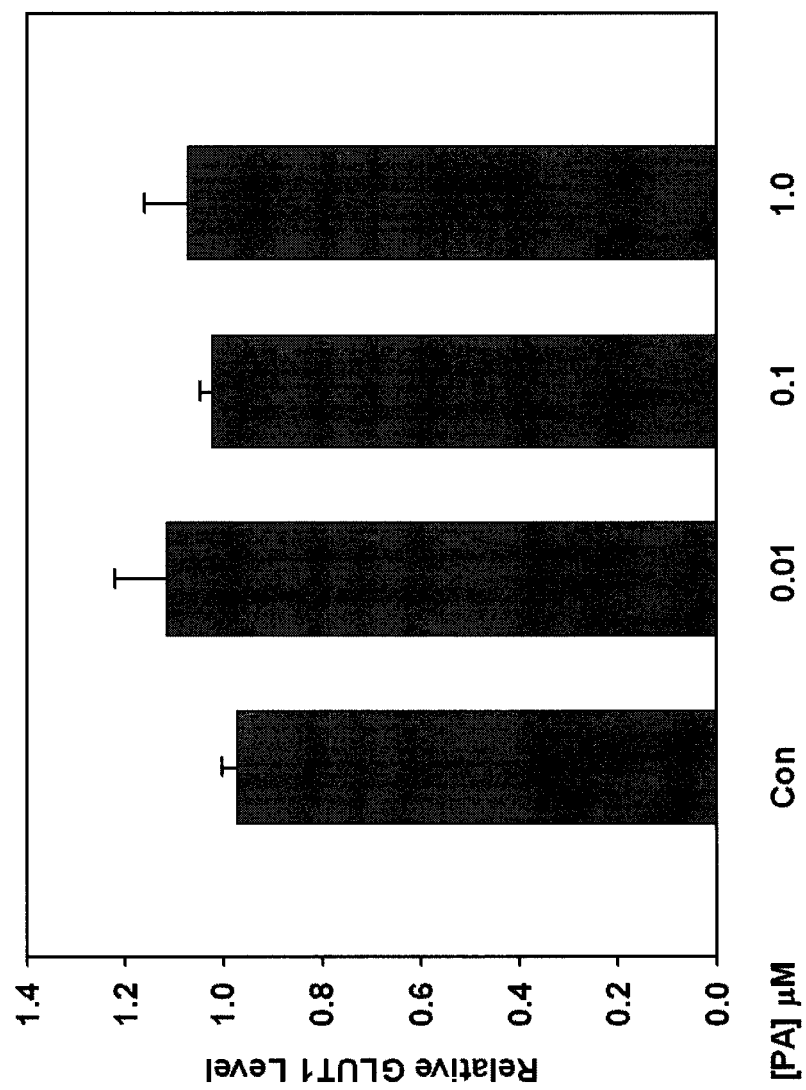
FIG. 5A is a plot that shows PA was not effective for enhancing the expression of GLUT1.
Figure 5B:
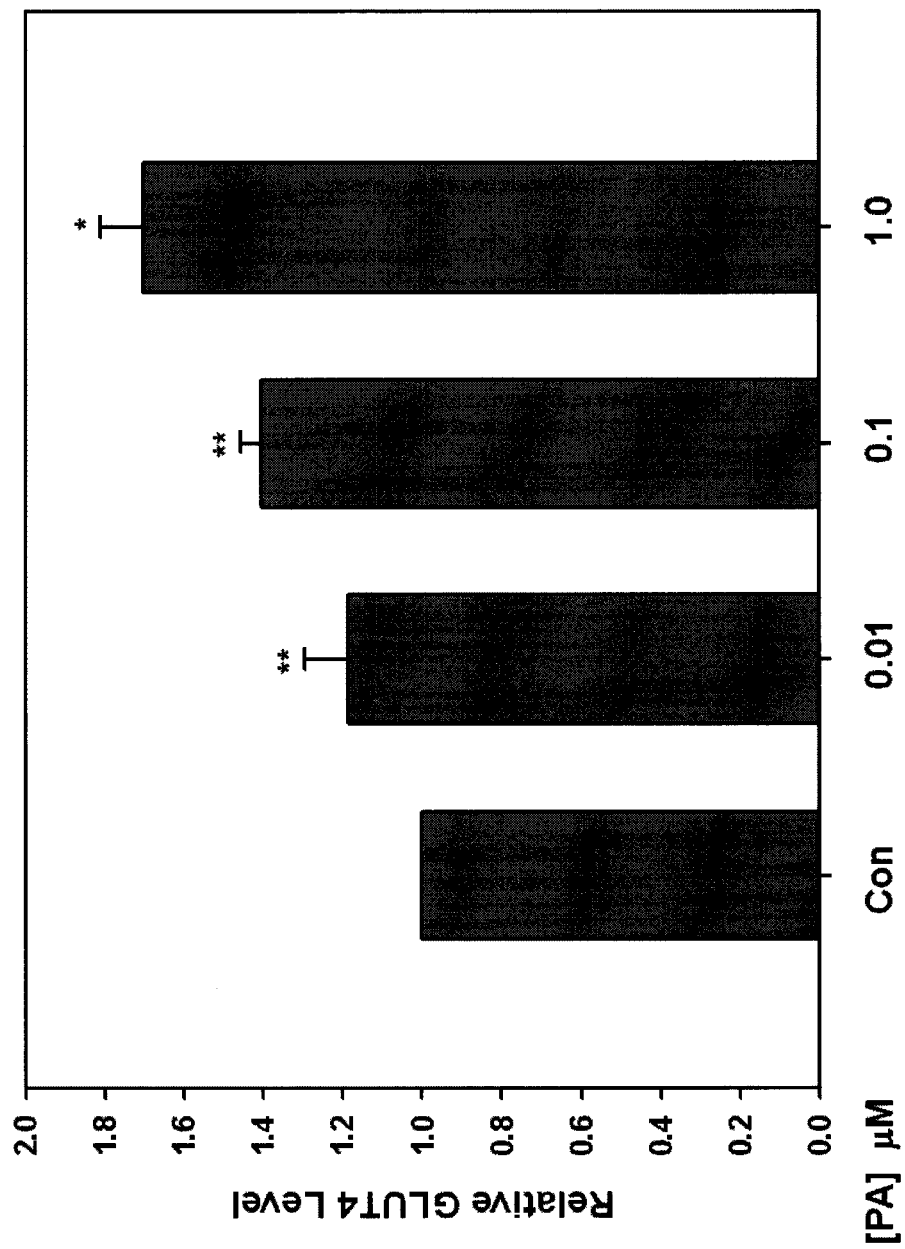
FIG. 5B is a graph that shows PA was effective for enhancing the expression of GLUT4. Differentiated mature cells were treated with different concentrations of PA for 24 hours, and then expressions of GLUT1 and GLUT4 were analyzed. The figures are shown as mean±SD (n=3). The symbol * is used to indicate p<0.05, and ** means p<0.01, in comparison with the control group (untreated).

(2) The Effects of PA, a Triterpene Compound; on Enhancing the Protein and mRNA Expression of GLUT4 in Mature Adipocytes FIG. 5 showed that when different doses of PA were administered to the mature adipocytes for 24 hours, and followed by performing the Western blot analysis targeting GLUT 1 and 4 to evaluate the effects of PA on the protein expression of GLUT 1 and 4; the results indicated that PA was effective for enhancing the protein expression of GLUT4 (FIG. 5A), but not for GLUT1 (FIG. 5B).

Figure 6:
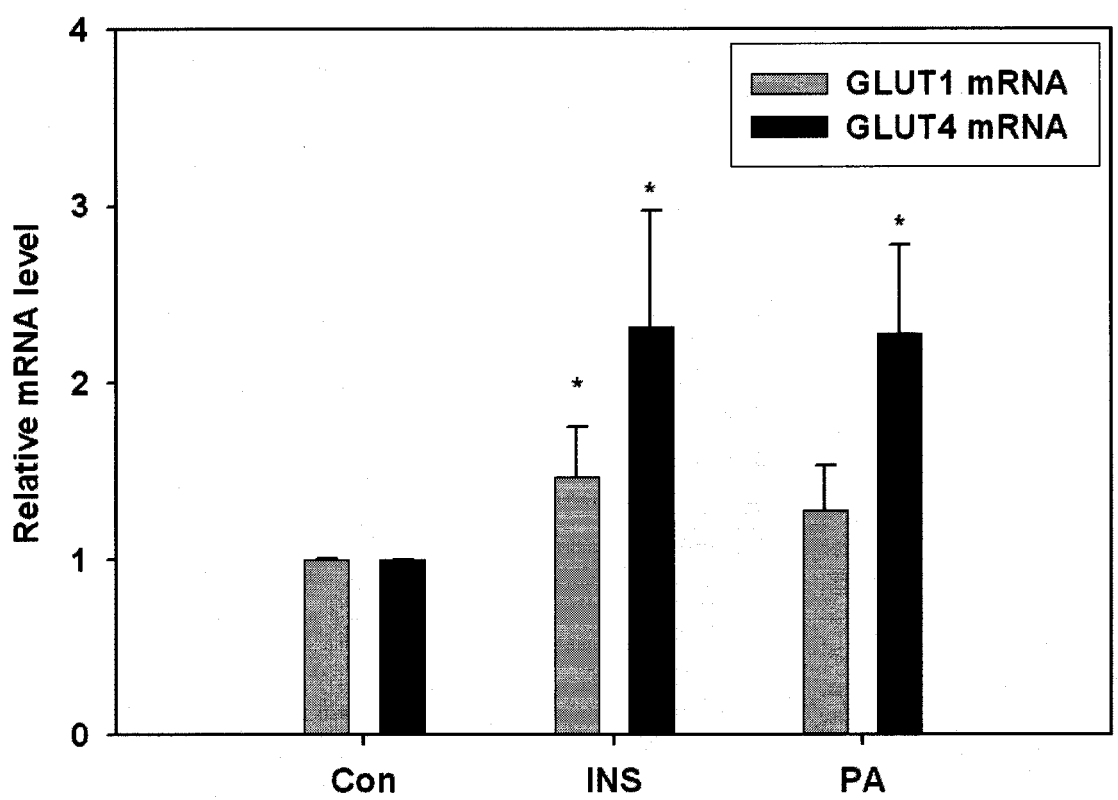
FIG. 6 is a plot that shows PA was effective for enhancing the mRNA expression of GLUT4, wherein the differentiated mature cells were separately treated with insulin (0.1 μM) and PA (0.01 μM) for 24 hours, and then mRNA expressions of GLUT1 and GLUT4 were analyzed. The figures are shown as mean±SD (n=3). The symbol * is used to indicate p<0.05, and ** means p<0.01, in comparison with the control group (untreated).
Figure 7A:
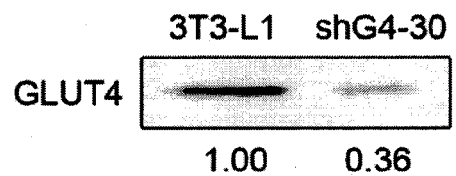
FIGS. 7A and 7B are diagrams that show PA was not effective for enhancing sugar uptake in adipocytes with suppressed mRNA expression of GLUT4. Mature adipocytes and adipocytes with suppressed mRNA expression of GLUT4 (shG4-30) were treated with different concentrations of PA and insulin, and then the GLUT4 expression (FIG. 7A) and its effects on sugar uptake (FIG. 7B) were analyzed. The figures are shown as mean±SD (n=6). The symbol * is used to indicate p<0.05, and ** means p<0.01, in comparison with the control group (untreated).
Figure 7B:
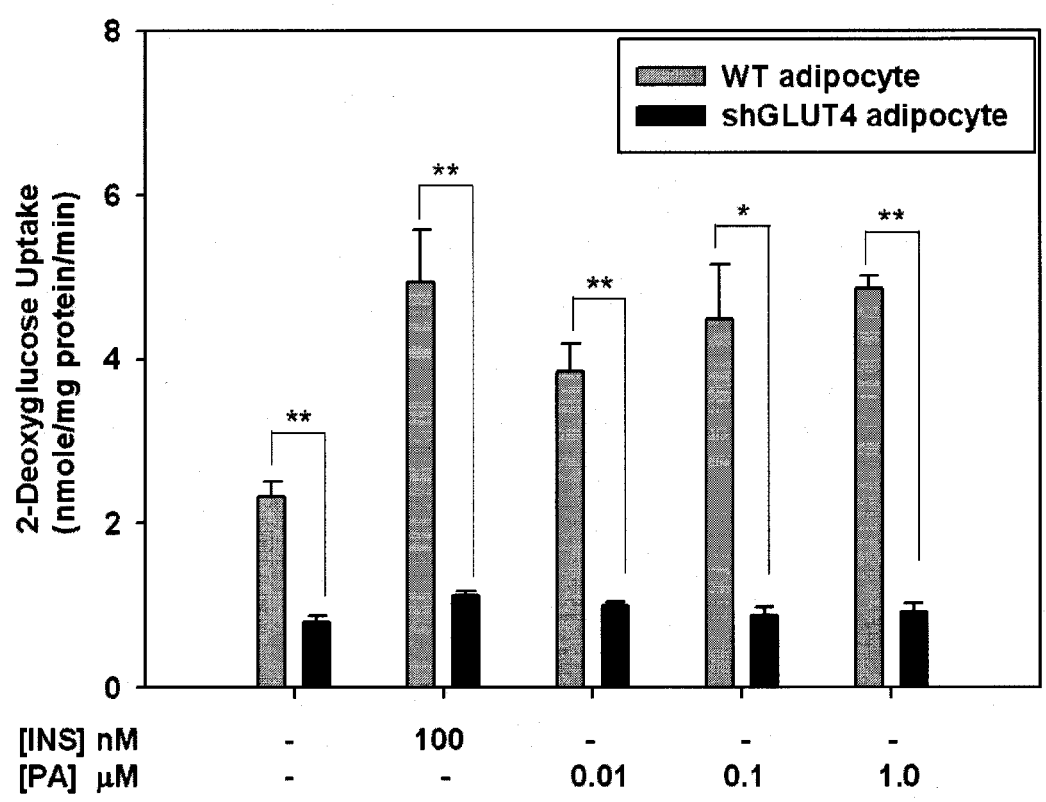

The results of using Q-PCR and a specific probe to investigate the effects of different concentrations of PA on the mRNA expression of GLUT proteins in mature 3T3-L1 adipocytes were shown in FIG. 6, and it revealed that 1 μM of PA could elevate the gene expression of GLUT4 to 228%, which suggested PA could regulate the gene and protein expression of GLUT4. Moreover, the mRNA-interfering method was used to create 3T3-L1 adipocytes with consistently low expression of GLUT4 (FIG. 7A), and the adipocytes was used to further evaluate glucose uptake, with the results shown in FIG. 7B, which demonstrated that different doses of PA did not greatly enhance the glucose uptake in the adipocytes, thereby proving that PA enhances glucose uptake by directly affecting GLUT4 expression.

Figure 8A:
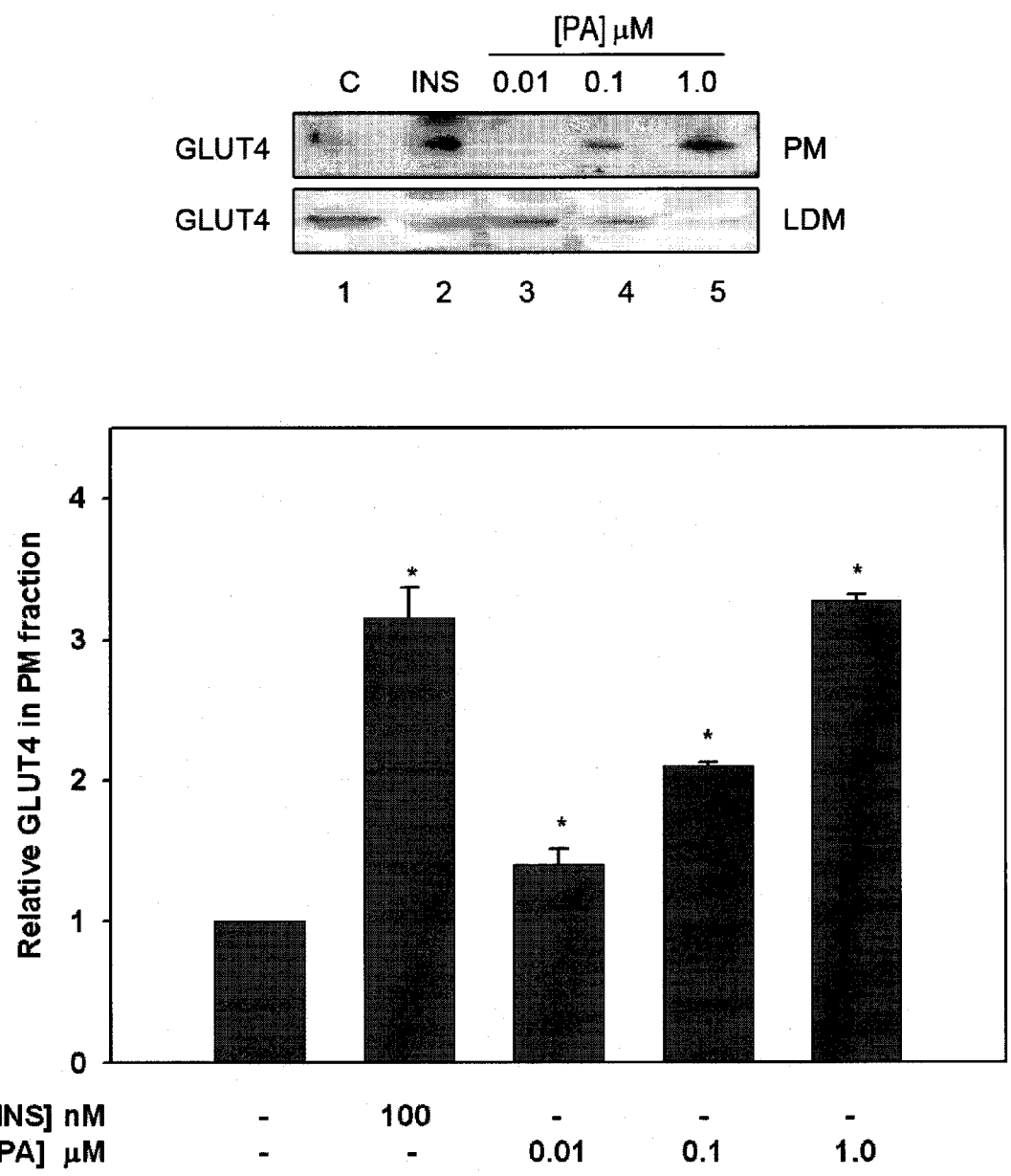
FIG. 8A is a diagram that shows GLUT4 proteins from different layers of cell membrane obtained by centrifugation for analysis, which indicates that PA was effective for enhancing the translocation of GLUT4 from intracellular organelles to the cell membrane.
Figure 8B:
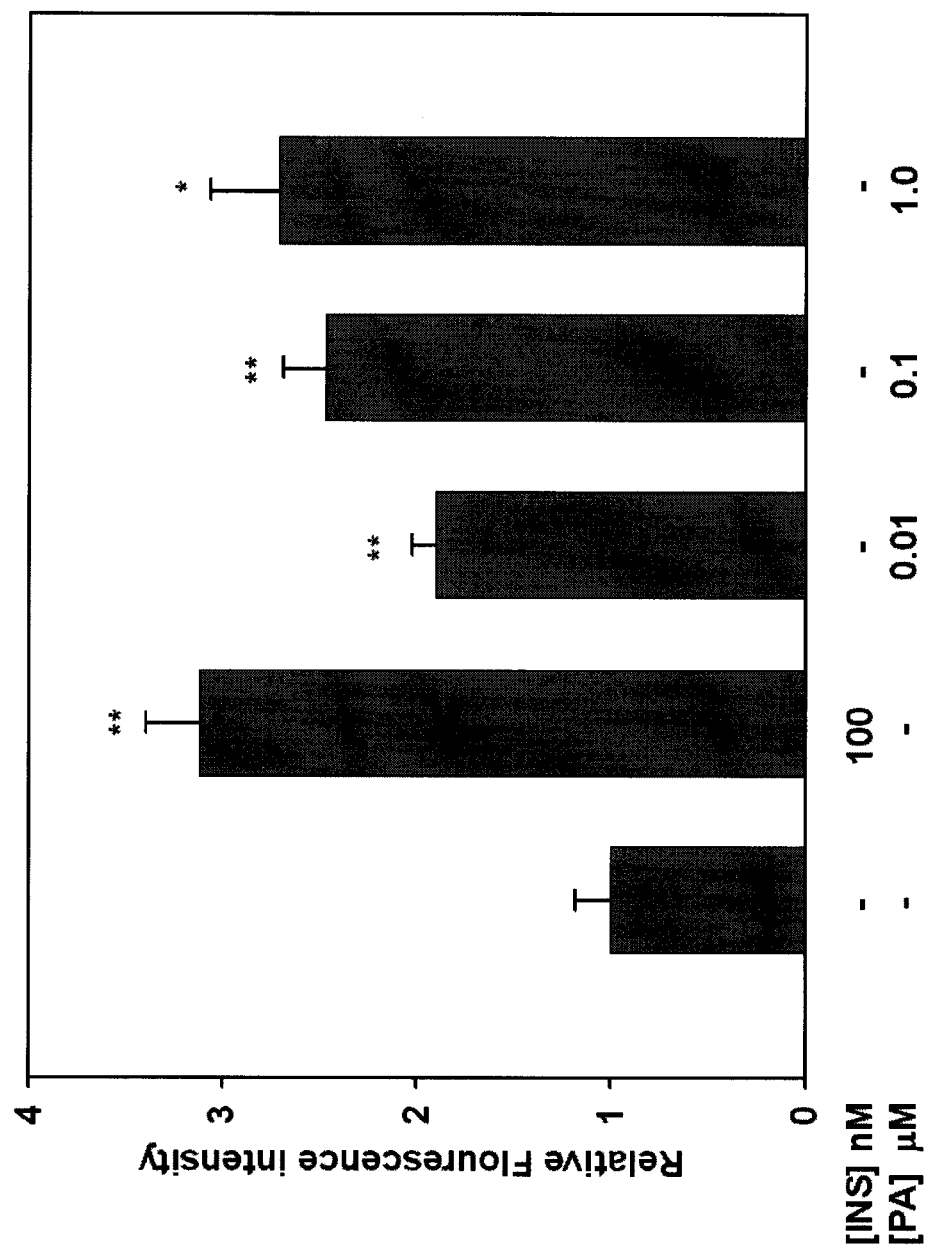
FIG. 8B is a plot that shows the analysis of GLUT4 from layers of cell membrane in a whole cell by fluorescence analysis, which indicates that PA was effective for enhancing the translocation of GLUT4 from intracellular organelles to the cell membrane. The figures are shown as mean±SD (n=3) for FIG. 8A and (n=6) for FIG. 8B. The symbol * is used to indicate p<0.05, and ** means p<0.01, in comparison with the control group (untreated).

(3) The Effects of PA on Enhancing the Translocation of GLUT4 from Intracellular Organelles to Plasma Membrane in Mature Adipocytes One of the mechanisms for insulin to enhance glucose uptake is to promote the translocation of a large number of GLUT4 from intracellular organelles to plasma membrane in order to carry out glucose uptake. Therefore, the mature 3T3-L1 adipocytes having the comprehensive system of insulin activating glucose uptake was employed to evaluate the translocation of GLUT4 proteins. FIG. 8A illustrated the results of Western blot analysis on the plasma membrane separated out using high-speed centrifugation, which revealed that 0.01 μM of PA significantly increased the amount of GLUT4 in the plasma membrane to 141%, and the amount was further increased to 328% when PA dose was elevated to 1 μM. The use of 3T3-L1 adipocytes stably expressing HA-GLUT4-GFP proteins and fluorescence measurement method further confirmed that PA enhances glucose uptake by increasing the translocation of GLUT4 to plasma membrane. It can be observed in FIG. 8B that when the dose of PA was added to 1.0 μM, the translocation of GLUT4 to plasma membrane was elevated 2.71-fold. The aforesaid results confirmed that PA is effective for enhancing the translocation of GLUT4 proteins to plasma membrane.

Figure 9A:
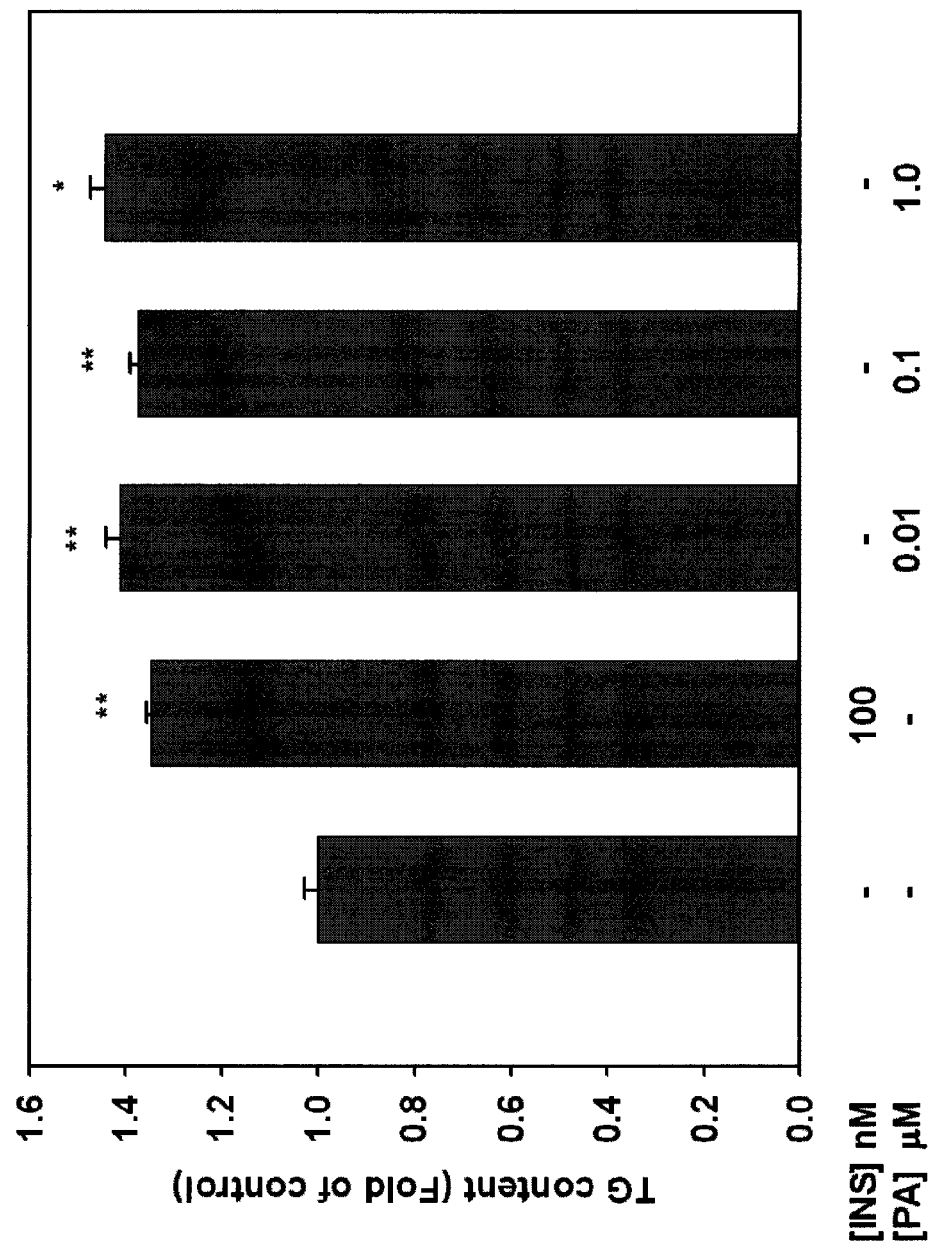
FIGS. 9A and 9B are plots that show PA was effective for enhancing the synthesis of triglycerides and inhibiting the breakdown of lipids (which gives rise to glycerol as the products) in the adipocytes. Mature adipocytes were treated with insulin (0.1 μM) and different concentrations of PA for 24 hours. The figures are shown as mean±SD (n=6). The symbol * is used to indicate p<0.05, and ** means p<0.01, in comparison with the control group (untreated).
Figure 9B:
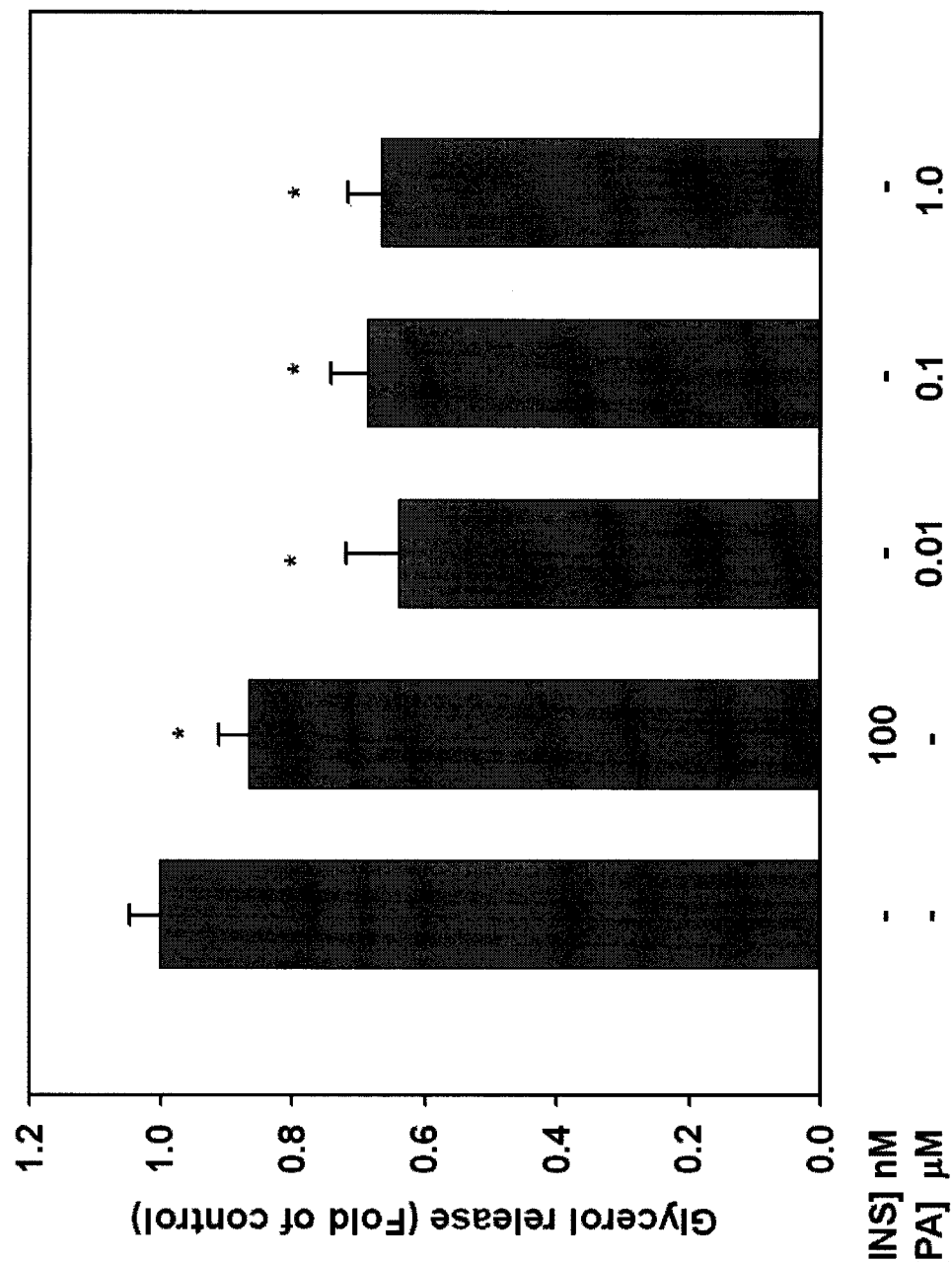

(4) The Effects of PA on Enhancing the Accumulation of Triglycerides and Reducing the Release of Glycerol into Culture Media in the Adipocytes In addition to observing the effects of PA on glucose uptake in adipocytes, the synthesis (storage) of triglycerides and lipid breakdown (release of glycerol) in adipocytes were also evaluated. FIGS. 9A and 9B showed the results from 24 hours after administering different doses of PA, and the accumulation of triglycerides was measured by Oil-Red O staining. It revealed that under the administration of PA, the accumulation of triglycerides exceeded 137%, and the release of glycerol was lowered to approximately 70% of the original level. The results suggested that PA was effective for promoting the synthesis of lipids and preventing the breakdown of lipids.

The present invention has been described with preferred examples thereof and it is understood that many changes and modifications to the described examples can be carried out without departing from the scope and the spirit of the invention that is intended to be limited only by the appended claims.

What is claimed is:

1. A method of treating type I diabetes, comprising administering to a mammal in need thereof an effective amount of a lanostane compound of the following formula (I), or a pharmaceutically acceptable salt thereof, said lanostane compound being the only active compound administered in the method for treating type I diabetes in the mammal,

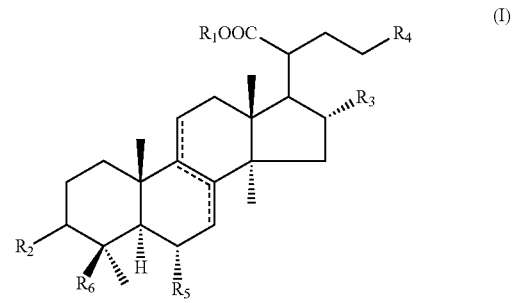

(I)

wherein $R_1$ is either —H or —CH$_3$; $R_2$ is —OCOCH$_3$, =O, or —OH; $R_3$ is —H or —OH; $R_4$ is —C(=CH$_2$)—C(CH$_3$)$_2$R$_a$, wherein $R_a$ is either —H or —OH, or —CH=C(CH$_3$)R$_b$, wherein $R_b$ is —CH$_3$ or —CH$_2$OH; $R_5$ is either —H or —OH, and $R_6$ is either —CH$_3$ or —CH$_2$OH.

2. The method of claim 1, wherein the lanostane compound (I) has the following chemical formula:

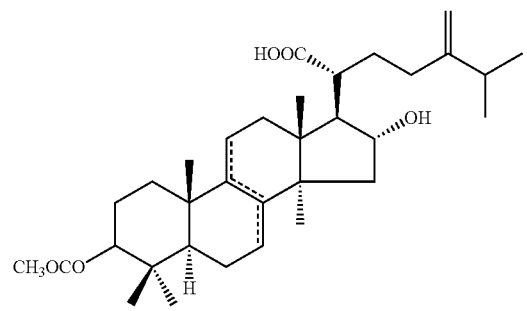

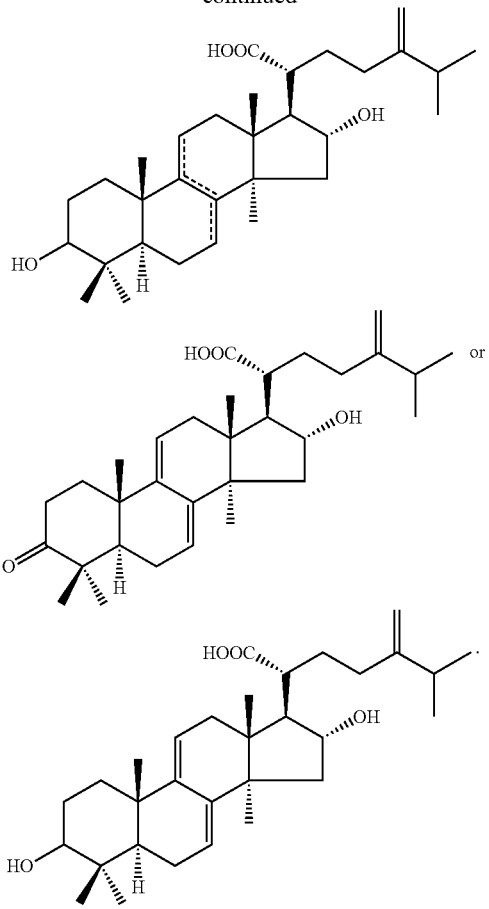

3. The method of claim 2, wherein the lanostane compound (I) has the following chemical formula:

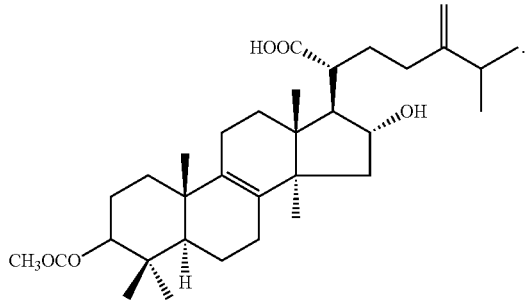

4. The method of claim 1, wherein the administering is injection.

5. The method of claim 1, wherein the administering is oral intake.

6. The method of claim 1, wherein the mammal is a human.

7. The method of claim 1, which comprises administering to the mammal an isolated lanostane compound having the formula (I) or a pharmaceutically acceptable salt thereof together with a pharmaceutical acceptable carrier or diluent.

8. A method of treating type I diabetes, comprising administering to a mammal in need thereof an effective amount of a Poria extract, wherein said Poria extract comprises, based on the weight of the Poria extract, 1-60% of a lanostane compound having the chemical formula (I) defined in claim 1, and said Poria extract is substantially free of secolanostane, said Poria extract being the only active ingredient administered in the method for treating type I diabetes in the mammal.

9. The method of claim 8, wherein said Poria extract comprises, based on the weight of the Poria extract, 5-35% of the lanostane compound (I).

10. The method of claim 8, wherein the lanostane compound (I) has the following chemical formula:

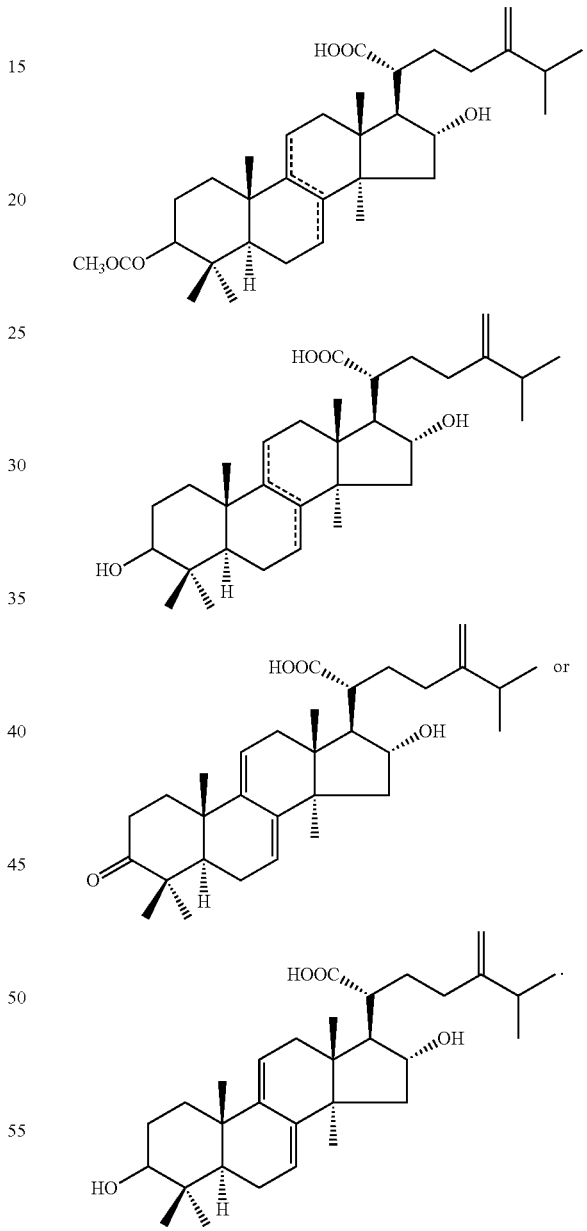

11. The method of claim 8, wherein the administering is oral intake.

12. The method of claim 8, wherein the mammal is a human.

13. A method of treating diabetes, consisting of administering to a mammal in need thereof an effective amount of a lanostane compound of the following formula, or a pharmaceutically acceptable salt thereof, said compound being the only active compound administered for treating type I diabetes in the mammal
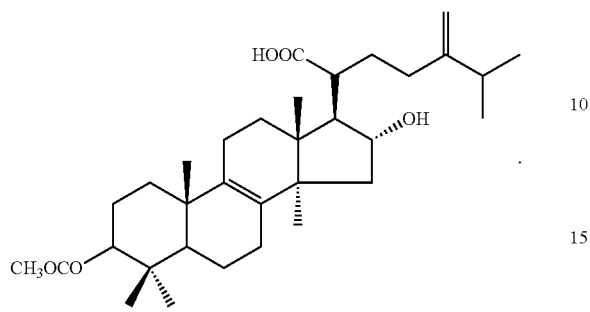
* * * * *